United States Patent
Quenet et al.

(10) Patent No.: US 7,359,749 B2
(45) Date of Patent: Apr. 15, 2008

(54) DEVICE FOR ANALYSIS OF A SIGNAL, IN PARTICULAR A PHYSIOLOGICAL SIGNAL SUCH AS AN ECG SIGNAL

(75) Inventors: Brigette Quenet, Paris (FR); M. Remi Dubois, Paris (FR); Yves Faisandier, Paris (FR)

(73) Assignee: ELA Medical S.A.S., Montrouge (FR)

( * ) Notice: Subject to any disclaimer, the term of this patent is extended or adjusted under 35 U.S.C. 154(b) by 662 days.

(21) Appl. No.: 10/712,976

(22) Filed: Nov. 13, 2003

(65) Prior Publication Data
US 2004/0162495 A1 Aug. 19, 2004

(30) Foreign Application Priority Data
Nov. 14, 2002 (FR) .................... 02 14212

(51) Int. Cl.
*A61B 5/04* (2006.01)
(52) U.S. Cl. ...................................... 600/509
(58) Field of Classification Search ................. 600/509
See application file for complete search history.

(56) References Cited

U.S. PATENT DOCUMENTS

| | | | |
|---|---|---|---|
| 5,623,935 A | 4/1997 | Faisandier | 128/696 |
| 5,680,866 A * | 10/1997 | Kangas et al. | 600/483 |
| 5,778,881 A | 7/1998 | Sun et al. | 128/696 |
| 6,309,342 B1 | 10/2001 | Blazey et al. | 600/26 |
| 6,705,990 B1 * | 3/2004 | Gallant et al. | 600/300 |
| 6,827,695 B2 * | 12/2004 | Palazzolo et al. | 601/41 |
| 2003/0074191 A1 * | 4/2003 | Byrnes et al. | 704/203 |
| 2005/0228591 A1 * | 10/2005 | Hur et al. | 702/19 |

FOREIGN PATENT DOCUMENTS

EP 1 219 237 A2 7/2002
WO 02/07594 A1 1/2002

* cited by examiner

*Primary Examiner*—George Manuel
*Assistant Examiner*—Christopher A. Flory
(74) *Attorney, Agent, or Firm*—Orrick, Herrington & Sutcliffe, LLP

(57) ABSTRACT

A device for analyzing a physiological signal, such as an electrocardiogram or electrogram, that was previously collected, filtered, sampled and digitized. The device memorizes the digitized signal and analyzes it by decomposing the signal into a plurality of N parameterized bump functions, where each bump function is a continuous function defined by three successive intervals, respectively, a first monotonic parameterized function, an affine function, and a second monotonic parameterized function, with one of the monotonic parameterized functions being increasing and the other decreasing. The parameterized functions are preferably half-Gaussian functions, and the affine function preferably has a null slope. Each N bump function is classified by recognizing at least one parameter characteristic of each wave, and allotting a standardized label, selected among a plurality of predetermined labels, according to one or to more of the characteristic parameters thus recognized.

20 Claims, 1 Drawing Sheet

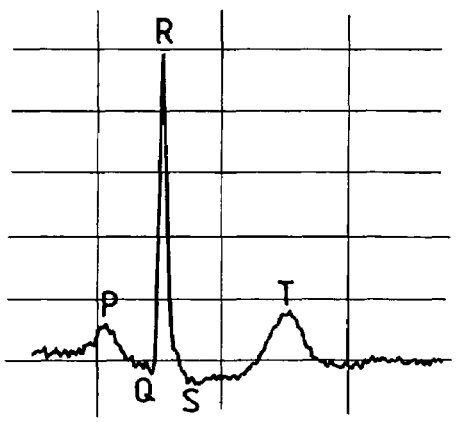
FIG_1
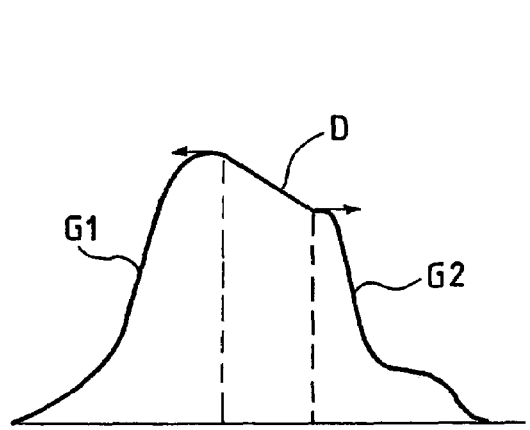
FIG_2
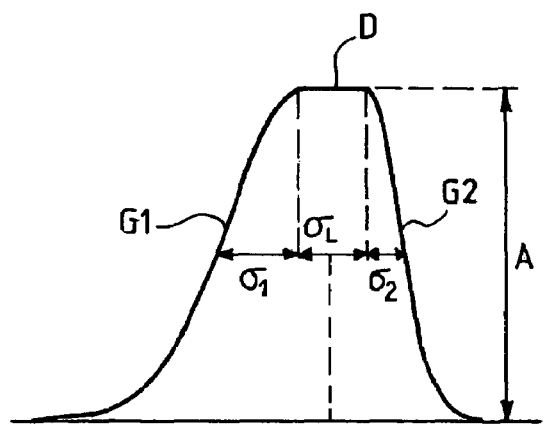
FIG_3
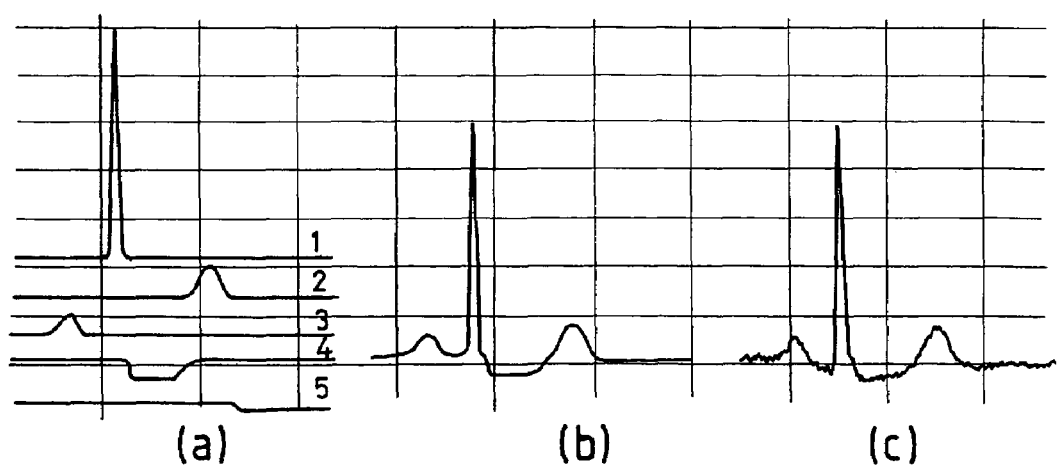
FIG_4

DEVICE FOR ANALYSIS OF A SIGNAL, IN PARTICULAR A PHYSIOLOGICAL SIGNAL SUCH AS AN ECG SIGNAL

FIELD OF THE INVENTION

The present invention is directed to the analysis of data, in particular of physiological data, for example, the data collected by an ambulatory active medical device or an active implanted medical device. An active medical device includes the devices defined in the Jun. 14, 1993, directive 93/42/CEE of the Council of the European Communities, and an active implantable medical device includes the devices defined in the Jun. 20, 1990, directive 90/385/CEE of the Council of the European Communities. The invention will be described with respect to an analysis of cardiac activity (electrocardiographic) signals, in particular of signals collected by a "Holter" recorder, i.e., an apparatus able to record signals without interruption over a long period, more specifically to record signals collected (sensed) using implanted electrodes (electrograms) or external electrodes (electrocardiograms), which signals which will be hereinafter collectively referred to as the "ECG signal." However, the invention is not restricted to the treatment of ECG signals, and can be more broadly applied to the analysis of other physiological parameters such as electroencephalogram, respiration rate, blood pressure, etc., and to non-physiological signals such as radar signals, ultrasonic signals, etc.

BACKGROUND OF THE INVENTION

The analysis of a Holter recording, i.e., recorded ECG signals, requires a rather complex examination. Indeed, the uninterrupted recording of an ECG signal of a patient over a 24 or 48 hour period represents approximately 100,000 PQRST complexes. It is thus necessary to analyze the variability of these complexes so as to search for any pathological event, such as a rhythm disorder, cardiac anoxia, operating anomaly of a cardiac pacemaker, etc. This analysis, which is typically carried out automatically by algorithms implemented in software executed in a computer (e.g., a microprocessor with associated memory, data registers, etc.) remote to an implanted device or included in an ambulatory apparatus, provides intermediate results, namely a synthesis of the data from which the doctor will be able to make a diagnosis.

These algorithms process a large volume of data. Therefore, a relatively large data processing means is required. As a result, the optimization of the algorithms, in terms of effectiveness compared to the required processor resources (e.g., memory size, speed, bit resolution, battery requirements as appropriate, etc.), is a significant factor in the field of the analysis of the physiological signals, and in particular with the Holter recording of signals.

Another difficulty with the known Holter recorder systems lies in the error rate in the analysis of the signals, which can have serious consequences, with in particular a risk of false diagnosis. Indeed, in the particular case of an ambulatory recorded ECG, the signal is not regular and numerous artifacts are present. More specifically, the ECG signal is generally made up of a signal that is cardiac in origin, almost periodic (namely, the so-called "PQRST" complex), accompanied by parasitic signals such as those generated by the muscles, by the mechanical disturbances on the electrode-skin interface, and by the electric or electromagnetic interference collected by the cables connecting the electrodes to the recorder.

The traditional algorithms are able to detect and filter out the parasitic signals, but not totally, and thus can lead to an error rate in the identification of the cardiac signal. Even if the traditional algorithms are able to reach typically an error rate of 0.1%, this represents approximately 100 errors during a 24 hour recording (approximately 100,000 PQRST complexes). It constitutes an error level still considered too high. This is because these errors can be concomitant with complexes presenting singularities that are significant from the point of view of making an appropriate diagnosis.

In addition, for an ECG signal, it is significant to be able to observe the variability of the QRS complex, which can be very meaningful for making a diagnosis. The analysis algorithm used must thus be able to reveal and discriminate a certain number of micro-variations.

The automatic analysis of an ECG signal generally comprises three distinct stages, which are: 1) the preliminary conditioning and filtering of the signal, so as to eliminate a certain number of parasites in the frequency field and to deliver a better quality signal; 2) the decomposition and identification of the characteristic waves of the signal; and 3) a synthesis of the temporal evolution of the parameters describing these various characteristic waves. These results make it possible for the doctor to establish a diagnosis, and it is obvious that the analysis results must be at the same time reliable and relevant to facilitate this diagnosis.

The reliability rests partly on the robustness and the good adaptation of the decomposition and the identification realized at the second stage. More particularly, the ECG signal is presented in the form illustrated on FIG. 1, which is a tracing representing the evolution over time of the electrical activity of the heart, with a succession of waves, having a positive or negative amplitude, on both sides of a line characteristic of the cardiac phase of rest known as "isoelectric line." During a normal cardiac beat (illustrated on FIG. 1), these positive or negative waves are identified as resulting from well defined physiological processes, making it possible to allot to each wave a standardized label, typically P, Q, R, S or T. Physiologically, the P wave is generated by the depolarization of the atrium, the QRS waves by the depolarization of the ventricle, and the T wave by the re-polarization of the ventricle. Based on the form and of the temporal position of these various waves, as well as their variability, the doctor will be able to recognize a given pathology.

Several processes of decomposition and identification of the characteristic waves of the signal have been proposed. One, a frequency analysis, makes it possible to describe the signal in the Fourier space (i.e., a transformation of the data acquired in the time domain to data in a frequency domain). However, such a decomposition is not completely adapted to the analysis of an ECG signal because this signal is not rigorously periodic. It has rich spectral contents that vary in time. Moreover, the sinusoidal functions of the frequency decomposition do not make it possible to obtain the phase of the signal, which is necessary to an identification of the component waves; indeed misadaptations that occur with such a frequency decomposition may lose the temporal phase information.

To carry out a time-frequency decomposition, one proposed technique is to use the transform in non-orthogonal wavelets, the identification of the waves then being done on the time-frequency content of the wavelets that model the signal. However, this method has a lack of resolution that quickly becomes a limit for a fine analysis. This difficulty can be mitigated by a decomposition in non-orthogonal wavelets (or in basic radial functions, or Gaussian, etc.). In this regard, the ECG signal is decomposed into a Gaussian sum which are of either a fixed or adaptable size. This method has been used but suffers from a characteristic handicap due to the fact that the waves to be modeled (i.e., the P, Q, R, S and T waves) are not really Gaussian, so that their modeling requires the use of a very great number of parameters to be of sufficient quality. This in turn requires considerable computing power to be able to be implemented in a reasonable time. Moreover, if the result is correct for QRS wave, then the P wave and the T wave, which are not easily comparable to a Gaussian distribution, are rather badly modeled: one must then use a great number of parameters to obtain a sufficient quality, thus leading to an excessive complexity of the analysis algorithm.

In view of the various issues, it also is known to use a simple linear decomposition, where the fluctuations of amplitude are replaced by straight line segments as soon as the derivative of the signal becomes significant. The result is a modeled signal made up of a succession of straight line segments that are then very simple to treat: For example, a monophasic wave is made of a succession of two segments of opposite directions, and a biphasic wave is made of three segments of opposite directions. This last technique is very effective, but reaches its limits when it applies to particular cases such as, for example, pertubating low frequency waves that lead to an over-decomposition in multiple segments that are then difficult to analyze.

OBJECTS AND SUMMARY OF THE INVENTION

It is an object of the present invention to propose a device for analyzing a signal, in particular a physiological signal previously collected by an active medical device, that can, in particular in the case of a ECG signal, mitigate the disadvantages of the analysis techniques used heretofore.

It is another object of the present invention to propose a device that, having an effectiveness at least equal to that of the best known techniques developed, can be used with more limited data-processing resources (i.e., relatively less memory resources and a lower power processor), for example, those data processing resources that are available with a conventional office or traditional portable computer. Such a device will permit a physician to have the results of the automatic analysis in a very short time period, typically a few minutes, after the transfer into the computer of the data previously memorized in the Holter recorder.

To this end, the invention broadly concerns a signal analyzing device of the above mentioned type, i.e., a device for analyzing a signal whose variations define a monodimensional function, this signal having beforehand been previously conditioned (i.e., filtered and made of better quality) and sampled and digitized. Such a device includes means for memorizing (storing in a memory) the digitized signal, and means for analyzing the memorized signal, with an extracting means that is able to decompose the memorized signal into a plurality of N elementary waves, and classifying means able to recognize at least one characteristic parameter of each elementary wave, thereby to allot a standardized label, selected among a plurality of predetermined labels, according to one or more of the aforesaid characteristic parameter(s) thus recognized.

According to the present invention, the extracting means operates to decompose the signal into N parameterized bump functions, where each bump function is a continuous function that is definite over three successive intervals by, respectively, a first monotonic parameterized function, an affine function, and a second monotonic parameterized function, wherein one of the aforementioned monotonic parameterized functions is an increasing function and the other is a decreasing function.

According to various advantageous subsidiary characteristics of the invention, the following variations may be optionally employed:

The dimension of the aforementioned monodimensional function is preferably a temporal dimension.

The aforementioned signal is preferably an ECG signal forming a wave of the PQRST type.

The aforementioned affine function is a function having a null slope, and each one of the aforesaid parameterized functions is half-Gaussian, one increasing and the other decreasing; the aforementioned characteristic parameters can be the five parameters constituting the standard deviation (sigma) of each of the two half-Gaussian functions, the length of the interval of definition of the affine part, the ordinate position of the interval, and the amplitude at the top of the Gaussian functions;

the extracting means includes a selecting means that is able to seek, for each of N elementary waves, a corresponding bump-type function selected from among a plurality of bump-type functions implemented in a library of predetermined bump-type functions, that is the most relevant in regards to the signal that is to be decomposed (i.e., the bump most closely approaching the original signal wave), and (include) means for adapting the parameters of each bump-type function thus determined by the selecting means, so as to minimize the variation between the signal and the composition of the N parameterized bump-type functions; more preferably the selecting means can perform its search by orthogonalisation of the aforementioned respective bump-type function that is the most relevant and/or by having the means for adapting adapt the aforementioned parameters by a non-linear optimization under constraints, e.g., three of the five parameters are positive.

the classifying means preferably operates by implementation of the so-called hidden Markov models.

In the embodiment indicated above where the signal is an ECG signal forming a wave of the PQRST type:

the means for analyzing the memorized signal preferably includes a subtracting means, able to withdraw from the memorized signal at least one of N elementary waves determined by the extracting means and carrying a given label, as the label is allotted by the classifying means;

the aforementioned N elementary waves are five (N=5), and the aforementioned predetermined labels are the P, Q, R, S and T waves of the ECG signal;

the ECG signal is a signal obtained by a known PCA analysis and projection of the principal components on a significant axis, in particular a dynamically computed axis of maximum amplitude;

the device includes means for determining the variability over time of at least one specific factor of at least one of the N elementary waves determined by the extracting means, in particular the amplitude of the T wave, the amplitude of the P wave or the direction of a significant axis as determined by PCA analysis; and the device includes means for determining a temporal correlation of a specific factor between at least two of the N elementary waves determined by the extracting means, in particular the temporal interval between a QRS wave and a T wave or the PR interval.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which:

FIG. 1, above mentioned, illustrates a representative PQRST complex of an ECG signal; or FIG. 2 illustrates the components of a representative bump function;

FIG. 3 illustrates the components and the corresponding parameters of a particular bump function advantageously used for the implementation of the invention; and FIGS. 4a, 4b and 4c show, respectively, the result of a decomposition carried out according to the invention, the composition of the N elementary waves giving the modeled signal, and the corresponding original signal.

DETAILED DESCRIPTION OF THE INVENTION

The origin of the invention lies in the creation of a fast and reliable algorithm that can be implemented with limited data-processing resources by operating the modeling of the physiological signal by a decomposition in "bumps," a bump being a well-known mathematical concept that, until now, has never proposed to be applicable to the analysis of a physiological signal.

A bump, as illustrated in FIG. 2, is a monotonic function that is parameterized such that it is defined by three successive intervals, a first increasing parameterized function G1, an affine function D, and a second decreasing parameterized function G2. According to the invention, the device for analyzing seeks to compose a set of bumps such that the graph of the sum of these bumps is as similar as possible to a known monodimensional signal. The optimization of the parameters of each bump is operated by any suitable mathematical method making it possible to obtain a graph as close as possible to the original signal to be modeled.

On FIG. 4, one thus illustrates, in the particular case of one beat of an ECG signal:

a) a set of bumps, in this example, elaborated in a manner that is described below.

b) the graph resulting from the composition of the five bumps, and c) the original signal which, as one can see it, is very close to the modeling obtained in (b).

Advantageously, one uses a particular type of bump, illustrated in FIG. 3, that is derived from the general definition given above in reference to FIG. 2. This particular type of bump is defined by a reduced number of parameters (five in this case) and, in practice, the obtained modeling proves extremely reliable and close to the original signal in the case of the analysis of a ECG signal, notwithstanding the reduced number of the parameters in the definition of the bump. For this purpose, one uses as affine part D of the bump a horizontal segment (i.e., a curve of null slope) and, in order to be able to carry out the stage of adaptation of the parameters by traditional algorithms of multidimensional optimization, the monotonic functions G1 and G2 are half-functions ones of equal amplitude A. Under these conditions, the bump is a continuous function, defined by five parameters and derivable compared to each one of these parameters, which are:

1) $\mu$: temporal position, for example, the ordinate position of the medium of the segment D;
2) $\sigma 1$: half standard deviation of first Gaussian G1;
3) $\sigma L$: length of the segment D;
4) $\sigma 2$: half standard deviation of second Gaussian G2; and
5) A: amplitude of the function The decomposition of the temporal signal into bumps is operated in an iterative manner in two stages:

1) Selection of the most relevant bump by a selection algorithm applied to a set of predetermined bumps preserved in a library of bump-types stored in computer memory. This selection stage can advantageously use a method of orthogonalisation in itself known (see, for example, J Korenberg, et al., "Orthogonal parameter estimate for non-linear stochastic systems," *International Journal of Control*, 48, 193-210, 1988).

2) Adaptation of the bump parameters which was selected at the preceding stage, i.e., research of the five parameters $\mu$, $\sigma 1$, $\sigma L$, $\sigma 2$, and A indicated above, so that the particular bump finally obtained approaches the original signal as much as possible to model it. This adaptation stage can advantageously use a method of nonlinear optimization under constraints, in itself known (see, for example, Minoux, *Programmation Mathématique* (1983), Dunod, 1983). Thus, modeling in N signal bumps will be made out of N time two stages. The maximum number N of bumps either is defined in advance, or dynamically adapted according to the precision of the required modeling. In the current case of an ECG signal, a heart beat modeled over five bumps proves in practice satisfactory: the limit of five bumps corresponds to the simple case where a bump represents a characteristic P, Q, R, S or T wave of the ECG recording, as illustrated on the FIG. 4a (FIG. 4b representing the modeled wave obtained by composition of the five bumps of FIG. 4a and FIG. 4c representing the original signal analyzed by the device of the invention).

The signal modeled in bumps is then analyzed to locate the characteristic waves of the cardiac activity. Each bump is then allotted a label (P, Q, R, S, T or other) according to its form and its location compared to the other bumps. One can advantageously use for this labellisation a method with hidden Markov chains (CMC or HMM, Hidden Markov Models), a method in itself known and described for example by L R Rabiner, "A Tutorial one Hidden Markov Models and Selected Applications in Speech Recognition", *Proceedings of the IEEE*, 77 (2), 257-286 (1989). This labeling of the bumps makes it possible to recognize the various components of a typical PQRST complex and thus to detect easily the atypical waves, which are those that, precisely, present the most interest for the diagnosis of the rate disorders.

Each wave of the ECG having been identified, it is then possible to measure each characteristic parameter of a given wave and—especially—to study it in a dynamic way. The curves obtained can be analyzed individually or in relation to other curves, because the modeling gives stabilized forms that allow effective correlations. One can thus analyze in a relevant way the variability of the T wave by the measurement of T wave amplitude variations and/or a temporal shift of the T wave compared to the QRS wave. One can also analyze the parameters of the bump representing the T wave, evaluate the variability of the PR interval, the amplitude of the wave P, etc.

The recognition of the waves also makes it possible to withdraw a known wave from a signal. This operation is very useful to uncover a wave of low amplitude (for example, the P wave) which occurs in a synchronous way in relation to a wave of large amplitude, for example, the Q, R, S or T waves. This automatic subtraction of a given wave from the signal makes it possible to reveal subjacent signals, for example, very early waves P, occurring just after the preceding QRS waves and which very often remained masked with the use of the prior known analysis techniques. The labellisation of the P waves provides results that will then make it possible for the doctor to improve the diagnosis considerably.

The example just described for implementing the invention can have many embodiments. Thus, rather than to model directly the signal collected on each ECG channel after filtering, it is advantageous to carry out, in a dynamic way (i.e., for each beat), a preliminary analysis of its principal components (hereinafter referred to as "PCA", or Principal Component Analysis). This technique, of itself known (see, for example, I. T. Jolliffe, *Principal Component Analysis*, Springer, 1986) concerns using the signals simultaneously obtained on channels X, Y and Z and recorded on several tracks, by seeking in a three-dimensional space a significant axis of maximum amplitude (PCA1 axis) and by expressing the temporal variation of the beat by its projection on this principal axis, whose position is computed with each beat. This pretreatment makes it possible in particular to model only the ECG on one track, containing the maximum of information, rather than on the set of original tracks.

The PCA of PQRST complex (and/or QRS complex and/or the P wave) makes it possible moreover to obtain permanently the plan of projection of the cardiac electric signals, which plan is related mainly to the position of the heart in space. An analysis of the movement of this plan or, more simply, of the axis of the principal component (PCA1 axis), makes it possible to obtain an image of the movement of the heart which can be used with various objectives such as:

1) the detection of breathing (which has the property to move the heart with each cycle), and the discrimination between thoracic or abdominal breathing; indeed, the displacement of the heart, intervening in axes or in different curves, results in a modulation of one or more angles of the principal components which, analyzed using adapted mathematical tools, allows the extraction of one or more curves of the breathing, for example, abdominal and thoracic;
2) the detection of the position of the body, with gravity causing anatomical changes that are transmitted to the heart and ECG signal;
3) the compensation of the deformations of the ECG signal introduced by the changes of position which move the heart: knowing the electric position, a dynamic matrix calculation applied to derivations XYZ or to the standard ECG derivations makes it possible to compensate for the influence of these changes and to recreate a stabilized signal. This stability is extremely useful for various analyses, in particular the comparisons between two recorded ECGs;
4) the creation of an original ECG by a spatial projection of the signal according to three components X, Y and Z. In relation to an XYZ ECG, this original ECG has two advantages, namely: (i) a very great stability, since it is not subjected to the variations of position of the heart, and (ii) a signal level that is a maximum in the first channel corresponding to the projection on the principal axis. It can be supplemented by the information on the angles of the projection axes, which then represent the positional changes of the heart, i.e., the effect of the body changes of position and of the breathing.

These various techniques resulting from PCA analysis in themselves are known, but the implementation of the invention makes it possible to largely improve the effectiveness, thanks in particular to the labeling of the bumps. The labeling of the bumps makes it possible to improve the effectiveness of this PCA-type analysis by carrying it out, if needed, on a particular wave.

Suitable devices for which the present invention has application include, for example, ambulatory Holter recorder and analyzer available from Ela Médical, Montrouge France. These devices are known under the trade marks Syneflash and Syneview.

In the case of implementation in an active implantable medical device such as an implantable pacemaker, such devices also are available from Ela Médical, Montrouge France. These devices are microprocessor-based systems having circuits for receiving, conditioning and processing detected electrical signals, and capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

We claim:

1. A medical device for analyzing a physiological signal having variations that define a monodimensional function, said physiological signal having been collected, filtered, sampled and digitized, comprising:
    means for memorizing the digitized physiological signal in a memory, and
    processor means for analyzing the memorized physiological signal, comprising:
        extracting means for decomposing the signal into a plurality of N parameterized bump functions, wherein each bump function is a continuous function having three successive intervals including a first monotonic parameterized function, an affine function, and a second monotonic parameterized function, one of said first second monotonic parameterized functions being an increasing function and the other being a decreasing function; and
        classifying means for recognizing at least one characteristic parameter of each N parameterized bump function, and allotting to said bump function a standardized label selected from among a plurality of predetermined labels, according to said at least one recognized characteristic parameter;
    means for storing the standardized label into memory;
    analyzing means for extracting abnormal signals indicating a pathological event or rhythm disorder from the analysis of said physiological signal;

means for transferring said abnormal signals to a computer display such that a physician can make a diagnosis of a condition based on said abnormal signals.

2. The device of claim 1 wherein said device comprises an active medical device and said signal is a physiological signal collected by said device.

3. The device of claim 1 wherein said monodimensional function comprises a temporal dimension.

4. The device of claim 3 wherein said signal is an electrocardiographic signal forming a wave of the PQRST type.

5. The device of claim 4 wherein said analyzing means further comprises a subtracting means for withdrawing from the memorized signal at least one of the determined N parameterized bump functions carrying an allotted label.

6. The device of claim 4 wherein said N parameterized bump functions further comprise five bump functions.

7. The device of claim 6 wherein said predetermined labels comprise the P, Q, R, S and T waves of said electrocardiographic signal.

8. The device of claim 7 wherein the device further comprises means for determining a variability over time of at least one specific factor of at least one of the determined N parameterized bump functions.

9. The device of claim 8 wherein said specific factor is selected from among an amplitude of the T wave, a temporal interval between the QRS wave and the T wave, a PR interval, an amplitude of the P wave, and a direction of a significant axis determined by a PCA analysis.

10. The device of claim 7 further comprising means for determining a temporary correlation of a specific factor between at least two of said determined N parameterized bump functions.

11. The device of claim 10 wherein said specific factor is selected from among an amplitude of the T wave, a temporal interval between the QRS wave and the T wave, a PR interval, an amplitude of the P wave, and a direction of a significant axis determined by a PCA analysis.

12. The device of claim 4 wherein said electrocardiographic signal comprises a signal obtained by a PCA analysis and projection of the principal components on a significant axis.

13. The device of claim 12 wherein said significant axis comprises a dynamically computed axis of maximum amplitude.

14. The device of claim 1 wherein said affine function is a function having a null slope.

15. The device of claim 1 wherein each of said monotonic parameterized functions comprises a half-Gaussian function.

16. The device of claim 1 wherein said affine function is a function having a null slope and said first and second monotonic parameterized functions are each a half-Gaussian function, and said characteristic parameters further comprise a set of five parameters selected from among the standard deviation of each of the two half-Gaussian functions, a definition interval length of the affine function, an ordinate position of said interval, and a peak amplitude of said half-Gaussian function.

17. The device of claim 1 wherein said extracting means further comprises:
a library containing a plurality of predetermined bump types;
means for selecting from said library, for each of said N parameterized bump functions, a bump type that is the most relevant in regard to the signal to be decomposed; and
means for adapting the parameters of each of the N selected bump-types and minimizing a variation between the signal and the composition of the parameterized N bump-types.

18. The device of claim 17 wherein the selecting means operates by an orthogonalisation of said selected most relevant bump-type.

19. The device of claim 17 wherein said adapting means performs a non-linear optimization under constraints of said parameters.

20. The device of claim 1 wherein said classifying means further comprises means for implementing hidden Markov models.

* * * * *